(12) United States Patent
Maeda et al.

(10) Patent No.: US 6,861,050 B2
(45) Date of Patent: Mar. 1, 2005

(54) METHOD OF PREVENTING DARKENING OF SKIN OR INHIBITING MELANIZATION OF MELENIN MONOMER AND POLYMERIZATION INHIBITOR OF BIOLOGICAL DIHYDROXYINDOLE COMPOUND

(75) Inventors: Kazuhisa Maeda, Yokohama (JP); Masato Hatao, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 10/162,738

(22) Filed: Jun. 6, 2002

(65) Prior Publication Data
US 2003/0134264 A1 Jul. 17, 2003

(30) Foreign Application Priority Data
Jun. 8, 2001 (JP) ........................ 2001-174555
Mar. 1, 2002 (JP) ........................ 2002-056360

(51) Int. Cl.[7] ............... A61K 7/42; A61K 7/44; A61K 7/00; A61K 31/34
(52) U.S. Cl. ............... 424/59; 424/60; 424/400; 424/401; 514/474
(58) Field of Search ................ 424/59, 60, 400, 424/401; 514/474

(56) References Cited

U.S. PATENT DOCUMENTS 4,876,084 A * 10/1989 Hori et al. .............. 424/62
4,981,680 A * 1/1991 Hori et al. .............. 424/62

FOREIGN PATENT DOCUMENTS

| JP | 8-134055 | 5/1996 |
| JP | 11-199425 A | 7/1999 |
| WO | WO 94/09756 A1 | 5/1994 |
| WO | WO 98/34591 A1 | 8/1998 |

OTHER PUBLICATIONS

Shigeru, "Cosmetic for Preventing Damage by Ultraviolet Ray," Patent Abstracts of Japan, vol. 1995, No. 06, Jul. 31, 1995, JP 07–082134, Mar. 28, 1995, Abstract.

Tomoko, "Skin–Beautifying Cosmetic," Patent Abstracts of Japan, vol. 017, No. 644, Nov. 30, 1993, JP 05–201847; Aug. 10, 1993, Abstract.

Database WPI, Section Ch, Week 200165, Derwent Publications Ltd., KR 2001 027 466, Apr. 6, 2001, Abstract, XP–002249722.

* cited by examiner

*Primary Examiner*—Shelly A. Dodson
(74) *Attorney, Agent, or Firm*—Foley & Lardner LLP

(57) ABSTRACT

A method of preventing darkening of the skin or inhibiting melanization caused by the irradiation of the melanin monomers with long wavelength ultraviolet rays having a wavelength of 320–400 nm as well as a polymerization inhibitor of a biological dihydroxyindole compound comprising 3-O-ethyl ascorbic acid and an external skin treatment composition containing the same.

6 Claims, No Drawings

METHOD OF PREVENTING DARKENING OF SKIN OR INHIBITING MELANIZATION OF MELENIN MONOMER AND POLYMERIZATION INHIBITOR OF BIOLOGICAL DIHYDROXYINDOLE COMPOUND

BACKGROUND OF THE INVENTION

1. Field of Invention

The present invention relates to a method of preventing darkening of the skin and a method of inhibiting pigmentation, more particularly relates to a method of preventing darkening of the skin and a method of inhibiting pigmentation by preventing melanization of melanin monomers due to ultraviolet rays.

The present invention also relates to a polymerization inhibitor for inhibiting the polymerization of biological dihydroxyindole due to long wavelength ultraviolet rays (UVA) by 3-O-ethyl ascorbic acid and an external skin treatment composition containing the same.

2. Description of the Related Art

In the past, darkening of the skin caused by ultraviolet rays was explained due to the higher activity of the enzyme tyrosinase in the melanocytes present in the basal layer of epidermis, the increase in the melanin produced from the tyrosine in the melanocytes, and the surrounding keratinocytes receiving the melanin. Therefore, as the method for preventing darkening of the skin caused by ultraviolet rays, kojic acid or arbutin etc. i.e., so-called whitening agents which inhibit the activity or synthesis of tyrosine in addition to ultraviolet ray blockers absorbing or scattering ultraviolet rays are used in the past.

The above process involves the production and synthesis of tyrosinase protein, and therefore it takes at least several days for the increase in the activity of tyrosinase and takes three to five days or so, until the surrounding keratinocytes receive the melanin and the skin appears dark.

However, since the darkening phenomenon caused by excessive exposure to the rays of the sun in leisure activities or while in the ocean occurs within a short time of one day, the present inventors believed that there was a mechanism of action different from the conventionally believed melanin production due to an enzymatic reaction involving tyrosine.

Therefore, we engaged in studies using a solar simulator with the aim of experimentally reproducing the darkening of skin occurring in one day. We divided the ultraviolet rays, which we are routinely exposed to, into medium wavelength ultraviolet rays (UVB: 280 to 320 nm) and long wavelength ultraviolet rays (UVA: 320 to 400 nm) and irradiated the forearms of human subjects with UVB or UVA to examine the changes in darkening over time. As a result, with irradiation by 300 mJ/cm$^2$ of UVB, the skin turned red within one day of the irradiation. This reddening continued for several days, then the skin gradually turned dark from 5 days. This darkness reached a peak on 7 days, and then gradually faded. On the other hand, with irradiation of 5 to 15 J/cm$^2$ of UVA, the skin turned dark immediately after irradiation, that is, immediate darkening occurred. This darkening faded after 3 hours. With irradiation of 16 to 45 J/cm$^2$, however, immediate darkening occurred after the end of the irradiation and this darkness lasted for over a week.

As a result of biochemical and histochemical investigation of the sustained darkening phenomenon due to UVA, we found that melanin is produced due to the relatively stable colorless, melanin monomers such as transparent compound dihydroxyindole carboxylic acid or its related compounds, by the melanocytes present in the base layer of the epidermis directly struck by the UVA.

SUMMARY OF THE INVENTION

The present invention was made based on the above finding. Namely, the objects of the present invention are to provide a method of preventing darkening of the skin and a method of inhibiting pigmentation based on a new mechanism of action.

In accordance with the first aspect of the present invention, there is provided a method of preventing darkening of the skin comprising inhibiting melanization of melanin monomers caused by the melanin monomers with ultraviolet rays.

In accordance with the second aspect of the present invention, there is provided a method of inhibiting pigmentation comprising inhibiting melanization caused by irradiation of melanin monomers with ultraviolet rays by an inhibitor of the melanization of melanin monomers.

In accordance with the third aspect of the present invention, there is provided a method of evaluating inhibitory action of melanization caused by ultraviolet rays comprising: irradiating a solution containing melanin monomers and a sample to be tested with ultraviolet rays; and using the extent of production of melanin after irradiation as an indicator of the melanization inhibitory action of the sample.

In accordance with the fourth aspect of the present invention there is provided inhibitors of melanization of melanin monomers caused by irradiating the melanin monomers with ultraviolet rays. The inhibitors include vitamin C or its derivative.

In accordance with the fifth aspect of the present invention there is provided an external skin treatment composition comprising including melanization inhibitors capable of inhibiting melanization of melanin monomers caused by irradiating the melanin monomers with ultraviolet rays.

The method of prevention of darkening of the skin, the method of inhibiting pigmentation, the method of evaluating the inhibitory action on melanization caused by irradiation of melanin monomers with ultraviolet rays, the melanization inhibitor, and external skin treatment compositions boasting inhibition of melanization of melanin monomers due to ultraviolet rays by including the same according to the present invention have been completely unknown up to now.

Furthermore, the present invention provides a polymerization inhibitor inhibiting polymerization of a biological dihydroxyindole compound (i.e., the compound in vivo) arising due to the irradiation of long wavelength ultraviolet rays (UVA) wherein the polymerization inhibitor comprises 3-O-ethyl ascorbic acid, and an external skin treatment composition including the same, in particular an external skin treatment composition for preventing immediate darkening.

The 3-O-ethyl ascorbic acid can inhibit the polymerization arising due to the biological dihydroxyindole in vivo caused by ultraviolet rays, whereby darkening of the skin was completely prevented. This is unknown up to now.

The 3-O-ethyl ascorbic acid usable in the present invention can be synthesized by ethoxylation of the hydroxyl group at the 3-position of ascorbic acid and further can be obtained as a commercial product from Nippon Hypox Lab. Inc. (Japanese Unexamined Patent Publication (Kokai) No. 8-134055).

DESCRIPTION OF THE PREFERRED EMBODIMENT

The constitution of the present invention will be explained in detail below.

According to the present invention, it is possible to prevent darkening of the skin by inhibiting melanization of melanin monomers occurring due to the melanin monomers being irradiated by ultraviolet rays.

The ultraviolet rays capable of being applied or capable of being used in the method of the present invention are 290 to 400 nm continuous or single wavelength ultraviolet rays of a fluorescent lamp, solar simulator, monochrometer, etc. Preferably, they are 320 to 400 nm UVA region ultraviolet rays.

The melanin monomers usable in the present invention include DHICA (i.e., 5,6-dihydroxyindole-2-carboxylic acid) or its salts, DHI (i.e., 5,6-dihydroxyindole), 6H5MICA (i.e., 6-hydroxy-5-methoxyindole-2-carboxylic acid), 5H6MICA (i.e., 5-hydroxy-6-methoxyindole-2-carboxylic acid), 6H5MI (i.e., 6-hydroxy-5-methoxyindole), 5H6MI (i.e., 5-hydroxy-6-methoxyindole), etc. Among these monomers, particularly DHICA (i.e., 5,6-dihydroxyindole-2-carboxylic acid) or its salts, is preferred.

The black-brown melanin produced by irradiation of ultraviolet rays can be evaluated using the naked eye, photographic assessment, the absorbance (e.g., 250 to 700 nm), ESR (i.e., electron spin resonance), etc. The method of evaluation of an inhibitor for black-brown melanin produced by melanin monomers due to ultraviolet rays is also possible by using similar substrates and evaluation methods.

According to the present invention, the melanization caused by irradiating the above melanin monomers with ultraviolet rays can be inhibited by a melanization inhibitor for melanin monomers. Here, as the melanization inhibitor, vitamin C or its derivatives can be exemplified.

The vitamin C or its derivatives include ascorbic acid esters such as sodium ascorbate, magnesium ascorbate phosphate ester (APM), ascorbyl aminopropyl phosphate, 2-sodium ascorbate sulfate ester, sodium ascorbate phosphate ester (APN), ascorbate stearate ester, ascorbate palmitate ester, ascorbate dipalmitate ester, and ascorbic acid ethers such as ascorbate-2-O-α-glucoside (AA-2G), ethoxylated ascorbic acid, ascorbyl tetra-2-hexyldecanate, ascorbyl glucosamine, etc.

The melanization inhibitor for black-brown melanin produced by melanin monomers due to ultraviolet rays of the present invention can not only be used as a whitener, but can also be used for improvement or prevention of skin conditions involving ultraviolet rays, in particular UVA.

Further, according to the present invention, an external skin treatment composition containing the above melanization inhibitors are provided.

The amount of the melanization inhibitor included in the external skin treatment composition of the present invention is 0.001 to 50.0% by weight, preferably 0.01 to 10.0% by weight, in the total weight of the external preparation. If the amount is less than 0.001% by weight, the desired effect in the present invention is not sufficiently exhibited, while if the amount is more than 50.0% by weight, preparation of a product is difficult, so these are not preferred. Further, even if the inhibitor is included in an amount of more than 10.0% by weight, the great improvement in the effect cannot be seen.

The dihydroxyindole compounds in the present invention include DHICA (i.e., 5,6-dihydroxyindole-2-carboxylic acid) or its salts, DHI (i.e., 5,6-dihydroxyindole), 6H5MICA (i.e., 6-hydroxy-5-methoxyindole-2-carboxylic acid), 5H6MICA (i.e., 5-hydroxy-6-methoxyindole-2-carboxylic acid), etc. Among these, particularly DHICA (i.e., 5,6-dihydroxyindole-2-carboxylic acid) or its salts, is preferred.

The polymerization inhibitor for polymerization (or melanization) of dehydroxyindole compounds caused by ultraviolet rays of the present invention can not only be used as a whitener, but can also be used for improvement or prevention of skin conditions involving ultraviolet rays, in particular UVA, for example, immediate darkening.

Further, according to the present invention, an external skin treatment composition containing the above polymerization inhibitor is provided.

The amount of the polymerization inhibitor in the external skin treatment composition of the present invention is 0.001 to 50.0% by weight, preferably 0.01 to 10.0% by weight, in the total weight of the external treatment composition. If the amount is less than 0.001% by weight, the desired effect of the present invention is not sufficiently exhibited, while if the amount is more than 50.0% by weight, preparation of a product is difficult, and therefore these are not preferred. Further, even if included in an amount of more than 10.0% by weight, the great improvement in the effect cannot be seen.

Further, the external skin treatment composition of the present invention may suitably include, in addition to the above essential ingredients, various conventional ingredients or additives normally used in cosmetics, quasi-pharmaceuticals, and pharmaceuticals as shown below.

That is, examples of the optional ingredients are moisture retaining agents such as glycerin, vaseline, urea, hyaluronic acid, and heparin, ultraviolet absorbents and scattering agents such as PABA derivatives (i.e., para-aminobenzoate acid, Escalol 507 etc.), cinnamic acid derivatives (Neoheliopan, Parsol MCX, Sunguard B, etc.), salicyclic acid derivatives (octyl salicylate etc.), benzophenone derivatives (ASL-24, ASL-24S, etc.), dibenzoylmethane derivatives (Parsol A, Parsol DAM, etc.), heterocyclic derivatives (Tinuvin-based etc.), and titanium oxide; metal sequestering agent such as disodium edetate, trisodium edetate, citric acid, sodium citrate, tartaric acid, sodium tartarate, lactic acid, malic acid, sodium polyphosphate, sodium metaphosphate, and gluconic acid; skin oil inhibitors such as salicyclic acid, sulfur, caffeine, and tannin; antiseptics and disinfectants such as benzalkonium chloride, benzetonium chloride, and chlorhexidine gluconate; anti-inflammatories such as diphenhydramine chloride, tranexamic acid, guaiazulene, azulene, allantoin, hinokitiol, glycyrrhizinic acid and its salts, glycyrrhizinic acid derivatives, and glycyrrhetinic acid; vitamins such as vitamin A, vitamin B group (B1, B2, B6, B12, B15), folic acid, nicotinic acids, pantothenic acids, biotin, vitamin D group (D2, D3), vitamin E, ubiquinones, and vitamin K (K1, K2, K3, and K4); amino acids and their derivatives such as asparagic acid, glutamic acid, alanine, lysine, glycine, glutamine, serine, cysteine, cystine, tyrosine, proline, arginine, pyrrolidone carboxylic acid, taurine, thiotaurin, and glutathione; whiteners such as retinol, tocopherol acetate, arbutin, kojic acid, ellagic acid, and placenta extract; antioxidants such as butylhydroxytoluene, butylhydroxyanisole, and propyl gallate; astringents such as zinc chloride, zinc sulfate, zinc carbolate, zinc oxide, and potassium aluminum sulfate; saccharides such as glucose, fructose, maltose, sucrose, trehalose, erythritol, maltose, xylitol, and lactitol; various plant extracts such as sugar cane, chamomile, horse chestnut, saxifrage, peony root, quince, scutellaria root, phellodendron bark, Japanese coptis, Huttuynia cordata, and ginkgo leaf; and also oil ingredients, surfactants, thickners, alcohols, powder ingredients, coloring materials, etc. may be suitably blended.

The "external skin treatment composition" of the present invention may be, for example, in the form of an ointment, cream, emulsion, lotion, pack, bath agent, or other product conventionally used for an external skin treatment composition. The form is not particularly limited. Further, the external skin treatment composition of the present invention is useful not only as a cosmetic, but also a pharmaceutical or quasi-pharmaceutical.

EXAMPLES

The present invention will now be explained in further detail by Examples. Note that the present invention is not limited by these Examples, the amounts blended are % by weight. Before the Examples, a test method relating to the effect of vitamin C and its derivatives of the present invention in inhibiting melanization of DHICA (i.e., 5,6-dihydroxyindole-2-carboxylic acid) due to ultraviolet rays and the results thereof will be explained.

(1) Method of Evaluation of Melanization of DHICA by Ultraviolet Rays

DHICA can be synthesized by a known method. 0.01 to 1.0 mg/ml of DHICA or its sodium salt is dissolved in water or a buffer such as phosphate buffer and 100 to 200 µl amounts distributed into microplate wells. A fluorescent lamp or solar simulator or monochrometer is used to irradiate this with ultraviolet rays for 10 minutes to 3 hours, then the absorbance at 405 nm is measured by a microplate reader to evaluate the amount of black-brown melanin.

(2) Method of Evaluation of Effect of Inhibition of Melanization of DHICA by Ultraviolet Rays 0.01 to 1.0 mg/ml of DHICA or its sodium salt is dissolved in water or a buffer such as a phosphate buffer and 100 to 200 µl amounts distributed into microplate wells. Compounds or plant extracts prepared at various concentrations are added in 1 to 100 µl amounts or before addition a fluorescent lamp or solar simulator or monochrometer is used to irradiate this with ultraviolet rays for 10 minutes to 3 hours, then the absorbance of 405 nm is measured by a microplate reader to evaluate the extent of black-brown melanin and evaluate the effect of the compound or plant extract.

(3) Measurement of Inhibitor for Melanization of DHICA by Ultraviolet Rays Containing Vitamin C and its Derivatives as Effective Ingredients The action of an inhibitor containing vitamin C and its derivatives as effective ingredients in inhibiting melanization of DHICA due to ultraviolet rays was evaluated by the following effect of inhibition of melanization of DHICA due to ultraviolet rays.

0.01 to 1.0 mg/ml of DHICA or its sodium salt is dissolved in water and 100 µl amounts distributed into microplate wells. 100 µl of ascorbic acid or its derivative adjusted to various concentrations was added and an FL-20BLB fluorescent lamp used to irradiate long wavelength ultraviolet rays. The absorbance at 405 nm was measured by a microplate reader to evaluate the amount of black-brown melanin and evaluate the effect of the compound. The results are shown in Table I-1.

TABLE I-1

| Tested substance | Sample concentration (%) | Rate of inhibition of UV-introduced melanization of DHICA (%) |
|---|---|---|
| Ascorbic acid | 0.1 | 70 |
| APM*1 | 0.1 | 20 |
| AA-2G*2 | 0.1 | 20 |
| 3-O-ethyl ascorbic acid | 0.1 | 80 |
| 3-O-ethyl ascorbic acid | 0.01 | 40 |

*1: Magnesium ascorbate phosphate ester
*2: Ascorbate-2-O-α-glucoside (4) Experiment of Actual Use for Investigating Effect of External Treatment Composition According to Present Invention in Inhibiting Skin Darkening The effects of application of external treatment compositions of the present invention to the skin were evaluated from the rate of prevention and rate of improvement of the degree of darkening of the skin color due to UVA. For the test, the arms of a panel of 30 healthy male and female subjects were used. Any two locations on the arms were set as test locations. The panel was divided into groups of 10 members each. Samples of the emulsions of the compositions (% by weight) shown in Table I-2 were coated in suitable amounts on one location, while the control was coated in a suitable amount at the other location. These were coated three times a day for 21 days. The test locations were irradiated with ultraviolet rays using an ultraviolet ray simulator (Solar Light Co., provided with WG 335 nm filter to cut UVB). The amount of irradiation of UVA by the apparatus used was 20 $J/cm^2$ which corresponded to about half to one-third of the average amount of UVA per sunny day in the summer since the average amount of UVA per sunny day in the summer is 40 to 60 $J/cm^2$. After irradiation, a suitable quantity was coated three times a day every day for 21 days. The skin color was measured using a Mexameter MX16 before and directly after irradiation, after 20 minutes, after 3 hours, after 1 day, after 7 days, after 14 days, and after 21 days. The efficacy was evaluated by the results of visually comparing the extent of darkening between the two locations at the times of measurement in five ranks and results of measurement by hardware. As samples, a 5% vitamin C-containing emulsion and a 5% AA-2G-containing emulsion were used as products of the invention, while a water-substituted emulsion was used as the comparative product. The results are shown in Table I-2.

TABLE I-2

| Sample | Product of invention | | Comparative product |
|---|---|---|---|
|  | 1 | 2 | 1 |
| Vitamin C | 5.0 | — | — |
| AA-2G | — | 5.0 | — |
| Water | — | — | 5.0 |
| Glycerin | 10.0 | 10.0 | 10.0 |
| 1,3-butyleneglycol | 4.0 | 4.0 | 4.0 |
| Ethanol | 7.0 | 7.0 | 7.0 |
| Polyoxyethylene (20) oleyl alcohol | 0.5 | 0.5 | 0.5 |
| Purified water | Balance | Balance | Balance |

TABLE I-2-continued

| Sample | Product of invention 1 | Product of invention 2 | Comparative product 1 |
|---|---|---|---|
| UVA darkening inhibitory effect | Very good | Very good | Fair |

As clear from Table I-2, the samples of the products of the present invention containing vitamin C or AA-2G exhibit a more superior inhibitory effect against darkening of the skin due to UVA than the sample of the comparative product.

Test methods relating to the effect of 3-O-ethyl ascorbic acid of the present invention in inhibiting black-brown melanosis of DHICA (i.e., 5,6-dihydroxyindole-2-carboxylic acid) due to ultraviolet rays and the results thereof will be explained.

(5) Measurement of Inhibitory Action for Melanization of DHICA by Ultraviolet Rays of Inhibitor Containing 3-O-Ethyl Ascorbic Acid as Effective Ingredient The action of an inhibitor containing 3-O-ethyl ascorbic acid as effective ingredients in inhibiting melanization of DHICA due to ultraviolet rays was evaluated by the following effect of inhibition of melanization of DHICA due to ultraviolet rays. 0.01 to 1.0 mg/ml of DHICA or its sodium salt is dissolved in water and 100 µl amounts distributed into microplate wells. 100 µl of ascorbic acid or its derivative adjusted to various concentrations was added and an FL-20BLB fluorescent lamp used to irradiate long wavelength ultraviolet rays. The absorbance at 405 nm was measured by a microplate reader to evaluate the extent of black-brown melanin and evaluate the effect of the compound. The results are shown in Table II-1.

TABLE II-1

| Tested substance | Sample concentration (%) | Rate of suppression of UV-induced melanization of DHICA (%) |
|---|---|---|
| 3-O-ethyl ascorbic acid | 0.1 | 80 |
| 3-O-ethyl ascorbic acid | 0.01 | 40 |
| AA-2G*1 | 0.1 | 20 |
| Ascorbic acid | 0.1 | 70 |

*1: Ascorbate-2-O-α-glucoside (6) Experiment of Actual Use for Investigating Effect in Inhibiting Skin Darkening Due to UVA The effects of application of external compositions of the present invention to the skin were evaluated from the rate of prevention and rate of improvement of the degree of darkening of the skin color due to UVA. For the test, the arms of a panel of 40 healthy male and female subjects were used. Any two locations on the arms were set as test locations. The panel was divided into four groups of 10 members each. Samples of the emulsions of the compositions (% by weight) shown in Table II-2 were coated in suitable amounts on one location, while the controls were coated in a suitable amount at the other location. These were coated three times a day for 21 days. The test locations were irradiated with ultraviolet rays using an ultraviolet ray simulator (Solar Light Co., provided with WG 335 nm filter to cut UVB). The amount of irradiation of UVA by the apparatus used was 20 J/cm² which corresponded to about half to one-third of the average amount of UVA per sunny day in the summer since the average amount of UVA per sunny day in the summer is 40 to 60 J/cm². The skin color was measured using a Mexameter MX16 before and directly after irradiation, after 20 minutes, after 3 hours, after 1 day, after 7 days, after 14 days, and after 21 days. The efficacy was evaluated by the results of visually comparing the extent of darkening between the two locations at the times of measurement in five ranks and results of measurement by hardware. As samples, a 5% 3-O-ethyl ascorbic acid-containing emulsion and a 1% 3-O-ethyl ascorbic acid-containing emulsion were used as products of the invention, while a 1% AA-2G (ascorbate-2-O-α-glucoside)-containing emulsion and 1% ascorbic acid-containing emulsion were used as the comparative products. The results are shown in Table II-2.

TABLE II-2

| Sample | Product of invention 1 | Product of invention 2 | Comparative product 1 | Comparative product 2 |
|---|---|---|---|---|
| 3-O-ethyl ascorbic acid | 5.0 | — | — | — |
| 3-O-ethyl ascorbic acid | — | 1.0 | — | — |
| AA-2G | — | — | 1.0 | — |
| Ascorbic acid | — | — | — | 1.0 |
| Water | — | 4.0 | 4.0 | 4.0 |
| Glycerin | 10.0 | 10.0 | 10.0 | 10.0 |
| 1,3-butyleneglycol | 4.0 | 4.0 | 4.0 | 4.0 |
| Ethanol | 7.0 | 7.0 | 7.0 | 7.0 |
| Polyoxyethylene (20) oleyl alcohol | 0.5 | 0.5 | 0.5 | 0.5 |
| Purified water | Bal. | Bal. | Bal. | Bal. |
| UVA darkening inhibitory effect | Very good | Very good | Good | Good |

As clear from Table II-2, the samples of the products of the present invention containing 3-O-ethyl ascorbic acid exhibit a more superior inhibitory effect against darkening of the skin due to UVA than the sample of the comparative product containing AA-2G or ascorbic acid.

Next, Examples of formulations of external skin treatment compositions according to the present invention will be given.

Example I-1

Cream

| Formulation | % by weight |
|---|---|
| Stearic acid | 5.0 |
| Stearyl alcohol | 4.0 |
| Isopropyl myristate | 18.0 |
| Glyceryl monostearate ester | 3.0 |
| Propylene glycol | 10.0 |
| Vitamin C | 0.01 |
| Caustic soda | 0.2 |
| Sodium hydrogensulfite | 0.01 |
| Preservative | q.s. |
| Perfume | q.s. |
| Ion exchanged water | Balance |

Preparation Method

The propylene glycol, vitamin C, and caustic soda were added to the ion exchanged water to dissolve them, then were heated and held at 70° C. (i.e., aqueous phase). The rest of the ingredients were mixed and heated to melt, then held at 70° C. (i.e., oil phase). The oil phase was gradually added to the aqueous phase. A little while after all finished being added, a reaction was caused while holding the mixture at that temperature. Next, the resultant product was homogeneously emulsified by a homomixer and then cooled to 30° C. while stirring well.

Example I-2

Cream

| Formulation | % by weight |
| --- | --- |
| Stearic acid | 2.0 |
| Stearyl alcohol | 7.0 |
| Hydrated lanolin | 2.0 |
| Squalane | 5.0 |
| 2-octyldodecyl alcohol | 6.0 |
| Polyoxyethylene (25) cetyl alcohol ether | 3.0 |
| Glyceryl monostearate ester | 2.0 |
| Propylene glycol | 5.0 |
| AA-2G | 0.05 |
| Sodium hydrogensulfite | 0.03 |
| Ethyl paraben | 0.3 |
| Perfume | q.s. |
| Ion exchanged water | Balance |

Preparation Method

The propylene glycol was added to the ion exchanged water and heated and held at 70° C. (i.e., aqueous phase). The rest of the ingredients were mixed and heated to melt then held at 70° C. (i.e., oil phase). The oil phase was added to the aqueous phase and the resultant mixture pre-emulsified and homogeneously emulsified by a homomixer, then the resultant product was cooled to 30° C. while stirring well.

Example I-3

Cream

| Formulation | % by weight |
| --- | --- |
| Solid paraffin | 5.0 |
| Beeswax | 10.0 |
| Vaseline | 15.0 |
| Liquid paraffin | 41.0 |
| Glyceryl monostearate ester | 2.0 |
| Polyoxyethylene (20) sorbitan monolaurate ester | 2.0 |
| Powdered soap | 0.1 |
| Borax | 0.2 |
| AA-2G | 0.05 |
| Sodium hydrogensulfite | 0.03 |
| Ethyl paraben | 0.3 |
| Perfume | q.s. |
| Ion exchanged water | Balance |

Preparation Method

The powdered soap and borax were added to the ion exchanged water and heated to dissolve and held at 70° C. (i.e., aqueous phase). The rest of the ingredients were mixed and heated to melt and held at 70° C. (i.e., oil phase). The oil phase was gradually added to the aqueous phase while stirring to cause the reaction. After the end of the reaction, the resultant mixture was homogeneously emulsified by a homomixer. After emulsification, the resultant product was cooled to 30° C. while stirring well.

Example I-4

Emulsion

| Formulation | % by weight |
| --- | --- |
| Stearic acid | 2.5 |
| Vaseline | 5.0 |
| Liquid paraffin | 10.0 |
| Polyoxyethylene (10) monooleate ester | 2.0 |
| Polyethylene glycol 1500 | 3.0 |
| Triethanolamine | 1.0 |
| Carboxyvinyl polymer (brandname: Carbopol 941, B. F. Goodrich Chemical Co.) | 0.05 |
| APM | 0.01 |
| Sodium hydrogensulfite | 0.01 |
| Ethyl paraben | 0.3 |
| Perfume | q.s. |
| Ion exchanged water | Balance |

Preparation Method

The carboxyvinyl polymer was dissolved in a small amount of the ion exchanged water (i.e., A phase). The polyethylene glycol 1500 and triethanolamine were added to the remaining ion exchanged water and heated to dissolve and held at 70° C. (i.e., aqueous phase). The rest of the ingredients were mixed and heated to melt and held at 70° C. (i.e., oil phase). The oil phase was added to the aqueous phase and the resultant mixture pre-emulsified, then the A phase was added and the mixture homogeneously emulsified by a homomixer. After emulsification, the resultant product was cooled to 30° C. while stirring well.

Example I-5

Emulsion

| Formulation | % by weight |
| --- | --- |
| Microcrystalline wax | 1.0 |
| Beeswax | 2.0 |
| Lanolin | 20.0 |
| Liquid paraffin | 10.0 |
| Squalane | 5.0 |
| Sorbitan sesquioleate ester | 4.0 |
| Polyoxyethylene (20) sorbitan monooleate ester | 1.0 |
| Propylene glycol | 7.0 |
| Vitamin C | 10.0 |
| Arbutin | 5.0 |
| Sodium hydrogensulfite | 0.01 |
| Ethyl paraben | 0.3 |
| Perfume | q.s. |
| Ion exchanged water | Balance |

Preparation Method

The propylene glycol was added to the ion exchanged water, then the mixture was heated and held at 70° C. (i.e., aqueous phase). The other ingredients were mixed and the mixture heated and melted and held at 70° C. (i.e., oil phase). The aqueous phase was gradually added to the oil phase while stirring the oil phase, then the mixture was homogeneously emulsified by a homomixer. After emulsification, the resultant product was stirred well and cooled to 30° C.

Example I-6

Gel

| Formulation | % by weight |
| --- | --- |
| 95% ethyl alcohol | 10.0 |
| Dipropylene glycol | 15.0 |
| Polyoxyethylene (50) oleyl alcohol ether | 2.0 |
| Carboxyvinyl polymer (brandname: Carbopol 940, B. F. Goodrich Chemical Co.) | 1.0 |
| Caustic soda | 0.15 |
| L-arginine | 0.1 |
| Vitamin C | 7.0 |
| Sodium 2-hydroxy-4-methoxy-benzophenone sulfonate | 0.05 |
| 3-sodium ethylene diamine tetraacetate · 2 hydrate | 0.05 |
| Methyl paraben | 0.2 |
| Perfume | q.s. |
| Ion exchanged water | Balance |

Preparation Method

The Carbopol 940 was homogeneously dissolved in the ion exchanged water, while the vitamin C and polyoxyethylene(50 mol)oleyl alcohol ether were dissolved then added to the aqueous phase. Next, the rest of the ingredients were added, then the solution was neutralized and thickened by caustic soda and L-arginine.

Example I-7

Beauty Lotion

| Formulation | % by weight |
| --- | --- |
| (A phase) | |
| Ethyl alcohol (95%) | 10.0 |
| Polyoxyethylene (20) octyl dodecanol | 1.0 |
| Pantothenyl ethyl ether | 0.1 |
| Vitamin C | 1.5 |
| AA-2G | 2.0 |
| Ethyl paraben | 0.15 |
| (B phase) | |
| Potassium hydroxide | 0.1 |
| (C phase) | |
| Glycerin | 5.0 |
| Dipropylene glycol | 10.0 |
| Sodium hydrogensulfite | 0.03 |
| Carboxyvinyl polymer (brandname: Carbopol 940, B. F. Goodrich Chemical Co.) | 0.2 |
| Purified water | Balance |

Preparation Method

The A phase and C phase were respectively homogeneously dissolved and the A phase was added to the C phase to solubilize it. Next, the B phase was added, then the mixture was filled.

Example I-8

Pack

| Formulation | % by weight |
| --- | --- |
| (A phase) | |
| Dipropylene glycol | 5.0 |
| Polyoxyethylene (60) hydrogenated castor oil | 5.0 |
| (B phase) | |
| Vitamin C | 0.01 |
| Olive oil | 5.0 |
| Tocopherol acetate | 0.2 |
| Ethyl paraben | 0.2 |
| Perfume | 0.2 |
| (C phase) | |
| Sodium hydrogensulfite | 0.03 |
| Polyvinyl alcohol (saponification value 90, polymerization degree 2,000) | 13.0 |
| Ethanol | 7.0 |
| Purified water | Balance |

Preparation Method

The A phase, B phase, and C phase were each homogeneously dissolved and the B phase added to the A phase for solubilization. Next, the C phase was added and then the mixture packed.

Example I-9

Solid Foundation

| Formulation | % by weight |
| --- | --- |
| Talc | 43.1 |
| Kaolin | 15.0 |
| Sericite | 10.0 |
| Zinc white | 7.0 |
| Titanium dioxide | 3.8 |
| Yellow iron oxide | 2.9 |
| Black iron oxide | 0.2 |
| Squalane | 8.0 |
| Isostearic acid | 4.0 |
| Monooleate POE sorbitan | 3.0 |
| Isocetyl octanate | 2.0 |
| Vitamin C | 0.5 |
| Preservative | q.s. |
| Perfume | q.s. |

Preparation Method

The powder ingredients from the talc to black iron oxide were sufficiently mixed in a blender, then the oil ingredients from the squalane to the isocetyl octanate, vitamin C, the preservative, and the perfume were added and mixed well.

The result was packed in a container and shaped.

Example I-10

Emulsion Type Foundation (Cream Type)

| Formulation | % by weight |
|---|---|
| (Powder Part) | |
| Titanium dioxide | 10.3 |
| Sericite | 5.4 |
| Kaolin | 3.0 |
| Yellow iron oxide | 0.8 |
| Bengara | 0.3 |
| Black iron oxide | 0.2 |
| (Oil Phase) | |
| Decamethyl cyclopentasiloxane | 11.5 |
| Liquid paraffin | 4.5 |
| Polyoxyethylene-modified dimethyl polysiloxane | 4.0 |
| (Aqueous Phase) | |
| Refined water | 50.0 |
| 1,3-butyleneglycol | 3.0 |
| Vitamin C | 1.0 |
| Tranexamic acid | 2.0 |
| Sorbitan sesquioleate ester | 3.0 |
| Preservative | q.s. |
| Perfume | q.s. |

Preparation Method

The aqueous phase was heated and stirred, then the sufficiently pulverized powder part was added and the mixture processed by a homomixer. The heated and mixed oil phase was then added and the mixture processed by the homomixer, then the perfume was added while stirring and the resultant product cooled to room temperature.

As explained above, the present invention finds for the first time a darkening phenomenon of skin due to UVA arising in melanin produced by colorless transparent melanin monomers produced by melanocytes present in the basal layer of epidermis being directly struck by UVA, and therefore, enables the effective prevention of darkening of the skin due to UVA.

Example II-1

Cream

| Formulation | % by weight |
|---|---|
| Stearic acid | 5.0 |
| Stearyl alcohol | 4.0 |
| Isopropyl myristate | 18.0 |
| Glyceryl monostearate ester | 3.0 |
| Propylene glycol | 10.0 |
| 3-O-ethyl ascorbic acid | 0.01 |
| Caustic soda | 0.2 |
| Sodium hydrogensulfite | 0.01 |
| Preservative | q.s. |
| Perfume | q.s. |
| Ion exchanged water | Balance |

Preparation Method

The propylene glycol, 3-O-ethyl ascorbic acid, and caustic soda were added to the ion exchanged water to dissolve them, then were heated and held at 70° C. (i.e., aqueous phase). The rest of the ingredients were mixed and heated to melt, then held at 70° C. (i.e., oil phase). The oil phase was gradually added to the aqueous phase. A little while after all finished being added, a reaction was caused while holding the mixture at that temperature. Next, the resultant product was homogeneously emulsified by a homomixer and then cooled to 30° C. while stirring well.

Example II-2

Cream

| Formulation | % by weight |
|---|---|
| Stearic acid | 2.0 |
| Stearyl alcohol | 7.0 |
| Hydrated lanolin | 2.0 |
| Squalane | 5.0 |
| 2-octyldodecyl alcohol | 6.0 |
| Polyoxyethylene (25) cetyl alcohol ether | 3.0 |
| Glyceryl monostearate ester | 2.0 |
| Propylene glycol | 5.0 |
| 3-O-ethyl ascorbic acid | 0.05 |
| Sodium hyaluronate | 0.1 |
| Sodium hydrogensulfite | 0.03 |
| Ethyl paraben | 0.3 |
| Perfume | q.s. |
| Ion exchanged water | Balance |

Preparation Method

The propylene glycol was added to the ion exchanged water and heated and held at 70° C. (i.e., aqueous water phase). The rest of the ingredients were mixed and heated to melt then held at 70° C. (i.e., oil phase). The oil phase was added to the aqueous phase and the resultant mixture pre-emulsified and homogeneously emulsified by a homomixer, then the resultant product was cooled to 30° C. while stirring well.

Example II-3

Cream

| Formulation | % by weight |
|---|---|
| Solid paraffin | 5.0 |
| Beeswax | 10.0 |
| Vaseline | 15.0 |
| Liquid paraffin | 41.0 |
| Glyceryl monostearate ester | 2.0 |
| Polyoxyethylene (20) sorbitan monolaurate ester | 2.0 |
| Powdered soap | 0.1 |
| Borax | 0.2 |
| 3-O-ethyl ascorbic acid | 0.05 |
| Acetylated sodium hyaluronate | 0.1 |
| Serine | 1.0 |
| Thiotaurine | 0.1 |
| Sodium hydrogensulfite | 0.03 |
| Trisodium edetate | 0.1 |
| Ethyl paraben | 0.3 |
| Perfume | q.s. |
| Ion exchanged water | Balance |

Preparation Method

The powdered soap and borax were added to the ion exchanged water and heated to dissolve and held at 70° C. (i.e., aqueous phase). The rest of the ingredients were mixed and heated to melt and held at 70° C. (i.e., oil phase). The oil phase was gradually added to the aqueous phase while stirring to cause the reaction. After the end of the reaction, the resultant mixture was homogeneously emulsified by a homomixer. After emulsification, the resultant product was cooled to 30° C. while stirring well.

Example II-4

Emulsion

| Formulation | % by weight |
|---|---|
| Stearic acid | 2.5 |
| Vaseline | 5.0 |
| Liquid paraffin | 10.0 |
| Polyoxyethylene (10) monooleate ester | 2.0 |
| Polyethylene glycol 1500 | 3.0 |
| Triethanolamine | 1.0 |
| Carboxyvinyl polymer (brandname: Carbopol 941, B. F. Goodrich Chemical Co.) | 0.05 |
| 3-O-ethyl ascorbic acid | 0.01 |
| Potassium 4-methoxy-salicyclate | 2.0 |
| Trimethyl glycine | 3.0 |
| Hypotaurine | 0.1 |
| Urea | 0.1 |
| Sodium hydrogensulfite | 0.01 |
| Ethyl paraben | 0.3 |
| Perfume | q.s. |
| Ion exchanged water | Balance |

Preparation Method

The carboxyvinyl polymer was dissolved in a small amount of the ion exchanged water (A phase). The polyethylene glycol 1500 and triethanolamine were added to the remaining ion exchanged water and heated to dissolve and held at 70° C. (i.e., aqueous phase). The rest of the ingredients were mixed and heated to melt and held at 70° C. (i.e., oil phase). The oil phase was added to the aqueous phase and the resultant mixture pre-emulsified, then the A phase was added and the mixture homogeneously emulsified by a homomixer. After emulsification, the resultant product was cooled to 30° C. while stirring well.

Example II-5

Emulsion

| Formulation | % by weight |
|---|---|
| Microcrystalline wax | 1.0 |
| Beeswax | 2.0 |
| Lanolin | 20.0 |
| Liquid paraffin | 10.0 |
| Squalane | 5.0 |
| Vitamin E acetate | 0.1 |
| Isostearic acid | 0.5 |
| Sorbitan sesquioleate ester | 4.0 |
| Polyoxyethylene (20) sorbitan monooleate ester | 1.0 |
| Betaine laurin dimethyl aminoacetate | 0.5 |
| Propylene glycol | 7.0 |
| 3-O-ethyl ascorbic acid | 10.0 |
| Arbutin | 5.0 |
| Sodium hydrogensulfite | 0.01 |

-continued

| Formulation | % by weight |
|---|---|
| Ethyl paraben | 0.3 |
| Perfume | q.s. |
| Ion exchanged water | Balance |

Preparation Method

The propylene glycol was added to the ion exchanged water, then the mixture was heated and held at 70° C. (i.e., aqueous phase). The other ingredients were mixed and the mixture heated and melted and held at 70° C. (i.e., oil phase). The aqueous phase was gradually added to the oil phase while stirring the oil phase, then the mixture was homogeneously emulsified by a homomixer. After emulsification, the resultant product was stirred well and cooled to 30° C.

Example II-6

Gel

| Formulation | % by weight |
|---|---|
| 95% ethyl alcohol | 10.0 |
| Dipropylene glycol | 15.0 |
| Polyoxyethylene (50) oleyl alcohol ether | 2.0 |
| Carboxyvinyl polymer (brandname: Carbopol 940, B. F. Goodrich Chemical Co.) | 1.0 |
| Caustic soda | 0.15 |
| L-arginine | 0.1 |
| 3-O-ethyl ascorbic acid | 7.0 |
| Sodium 2-hydroxy-4-methoxy-benzophenone sulfonate | 0.05 |
| Trisodium dihydrogen ethylene diamine tetraacetate | 0.05 |
| Methyl paraben | 0.2 |
| Perfume | q.s. |
| Ion exchanged water | Balance |

Preparation Method

The Carbopol 940 was homogeneously dissolved in the ion exchanged water, while the 3-O-ethyl ascorbic acid and polyoxyethylene(50 mol)oleyl alcohol ether were dissolved in the 95% ethanol and then added to the aqueous phase. Next, the rest of the ingredients were added, then the solution was neutralized and thickened by caustic soda and L-arginine.

Example II-7

Beauty Lotion

| Formulation | % by weight |
|---|---|
| (A phase) | |
| Ethyl alcohol (95%) | 10.0 |
| Dibutyl hydroxytoluene | 0.01 |
| Polyoxyethylene (20) octyl dodecanol | 1.0 |
| Pantothenyl ethyl ether | 0.1 |
| 3-O-ethyl ascorbic acid | 1.5 |

-continued

| Formulation | % by weight |
|---|---|
| AA-2G | 2.0 |
| Saxifrage extract | 0.1 |
| Scutellaria root extract | 0.1 |
| Methyl paraben | 0.15 |
| (B phase) | |
| Potassium hydroxide | 0.1 |
| (C phase) | |
| Glycerin | 5.0 |
| Dipropylene glycol | 10.0 |
| Sodium hydrogensulfite | 0.03 |
| Carboxyvinyl polymer | 0.2 |
| (brandname: Carbopol 940, B. F. Goodrich Chemical Co.) | |
| Sodium metaphosphate | 0.1 |
| Dye | q.s. |
| Purified water | Balance |

Preparation Method

The A phase and C phase were respectively homogeneously dissolved and the A phase was added to the C phase to solubilize it. Next, the B phase was added, then the mixture was filled.

Example II-8

Pack

| Formulation | % by weight |
|---|---|
| (A phase) | |
| Dipropylene glycol | 5.0 |
| Polyoxyethylene (60) hydrogenated castor oil | 5.0 |
| (B phase) | |
| 3-O-ethyl ascorbic acid | 0.01 |
| Olive oil | 5.0 |
| Tocopherol acetate | 0.2 |
| Ethyl paraben | 0.2 |
| Perfume | 0.2 |
| (C phase) | |
| Sodium hydrogensulfite | 0.03 |
| Polyvinyl alcohol (saponification value 90, polymerization degree 2,000) | 13.0 |
| Ethanol | 7.0 |
| Purified water | Balance |

Preparation Method

The A phase, B phase, and C phase were each homogeneously dissolved and the B phase added to the A phase for solubilization. Next, the C phase was added and then the mixture packed.

Example II-9

Solid Foundation

| Formulation | % by weight |
|---|---|
| Talc | 43.1 |
| Kaolin | 15.0 |
| Sericite | 10.0 |
| Zinc white | 7.0 |
| Titanium dioxide | 3.8 |
| Yellow iron oxide | 2.9 |
| Black iron oxide | 0.2 |
| Squalane | 8.0 |
| Isostearic acid | 4.0 |
| Monooleate POE sorbitan | 3.0 |
| Isocetyl octanate | 2.0 |
| 3-O-ethyl ascorbic acid | 0.5 |
| Preservative | q.s. |
| Perfume | q.s. |

Preparation Method

The powder ingredients from the talc to black iron oxide were sufficiently mixed in a blender, then the oil ingredients from the squalane to the isocetyl octanate, 3-O-ethyl ascorbic acid, the preservative, and the perfume were added and mixed well. The result was packed in a container and shaped.

Example II-10

Emulsion Type Foundation (Cream Type)

| Formulation | % by weight |
|---|---|
| (Powder Part) | |
| Titanium dioxide | 10.3 |
| Sericite | 5.4 |
| Kaolin | 3.0 |
| Yellow iron oxide | 0.8 |
| Bengara | 0.3 |
| Black iron oxide | 0.2 |
| (Oil Phase) | |
| Decamethyl cyclopentasiloxane | 11.5 |
| Liquid paraffin | 4.5 |
| Polyoxyethylene-modified dimethyl polysiloxane | 4.0 |
| (Aqueous Phase) | |
| Purified water | 50.0 |
| 1,3-butyleneglycol | 3.0 |
| 3-O-ethyl ascorbic acid | 1.0 |
| Tranexamic acid | 2.0 |
| Sorbitan sesquioleate ester | 3.0 |
| Preservative | q.s. |
| Perfume | q.s. |

Preparation Method

The aqueous phase was heated and stirred, then the sufficiently pulverized powder part was added and the mixture processed by a homomixer. The heated and mixed oil phase was then added and the mixture processed by the homomixer, then the perfume was added while stirring and the resultant product cooled to room temperature.

Example II-11

Sunscreen Emulsion (W/O Type Emulsion)

|  | % by weight |
|---|---|
| (Oil phase) | |
| Volatile cyclic silicone | 24.0 |
| Octyl methoxycinnamate | 7.0 |
| Titanium dioxide (hydrophobically treated) | 10.0 |
| Zinc oxide (hydrophobically treated) | 10.0 |
| Talc (hydrophobically treated) | 4.0 |
| Squalane | 5.0 |
| Dimethycone copolyol | 2.0 |
| Organic modified montmorillonite | 0.5 |
| Preservative | q.s. |
| Perfume | q.s. |
| (Aqueous phase) | |
| Refined water | 26.5 |
| Dipropylene glycol | 7.0 |
| 3-O-ethyl ascorbic acid | 1.0 |
| Arbutin | 3.0 |

Preparation Method

The oil phase and aqueous phase were respectively mixed and dissolved. The oil phase had the titanium dioxide sufficiently dispersed therein, then the aqueous phase was added. The mixture was emulsified using a homogenizer.

Example II-12

Liquid Cosmetic (and Sheet-Shaped Cosmetic Impregnated with Same)

|  | % by weight |
|---|---|
| (Aqueous phase) | |
| Glycerin | 10.0 |
| 1,3-butylene glycol | 5.0 |
| 3-O-ethyl ascorbic acid | 1.0 |
| Xanthan gum | 0.1 |
| Carboxyvinyl polymer | 0.1 |
| Citric acid | 0.1 |
| Sodium citrate | 0.2 |
| Lactic acid | 0.1 |
| Trisodium edetate | 0.1 |
| Refined water | Balance |
| (Alcohol phase) | |
| Ethanol | 10.0 |
| Polyoxyethylene polyoxypropylene decyltetradecyl ether | 1.0 |
| Perfume | q.s. |

Preparation Method

The aqueous phase and alcohol phase were respectively homogeneously dissolved, then the alcohol phase was added to the aqueous phase and the two homogeneously mixed.

Example II-13

Sunscreen

|  | % by weight |
|---|---|
| (Oil phase) | |
| Benton 38 (National Red Co.) | 2.0 |
| Isostearyl alcohol | 1.0 |
| Solid silicone | 10.0 |
| Trimethylsiloxysilicate | 5.0 |
| Hydrophobic titanium oxide | 5.0 |
| Octyl methoxycinnamate | 10.0 |
| Evening primrose oil | 0.3 |
| Spherical polyethylene | 1.0 |
| Tocopherol acetate | 0.3 |
| Vitamin A acetate | 0.1 |
| Perfume | q.s. |
| (Aqueous phase) | |
| 3-O-ethyl ascorbic acid | 1.0 |
| L-alanine | 0.5 |
| L-arginine hydrochloride | 1.0 |
| 1,3-butylene glycol | 5.0 |
| Methyl paraben | 0.2 |
| Xylitol | 8.0 |
| Purified water | Balance |

Preparation Method

The homogeneously dissolved aqueous phase parts were added to the homogeneously dispersed oil phase parts and the mixture was homogeneously dispersed by a homomixer to obtain a water-in-oil type emulsion composition.

Example II-14

W/O Emulsion Type Emulsion

|  | % by weight |
|---|---|
| Aqueous phase | |
| Isopropyl alcohol | 10.0 |
| Dipropylene glycol | 2.0 |
| Potassium chloride | 0.5 |
| Trisodium edetate | 0.1 |
| Diglyceryl diisostearate | 0.5 |
| POE modified dimethyl polysiloxane | 1.0 |
| 3-O-ethyl ascorbic acid | 2.0 |
| Methyl paraben | 0.1 |
| Ion exchanged water | Balance |
| (Oil phase) | |
| Octamethylcyclotetrasiloxane | 25.0 |
| Decamethylcyclopentasiloxane | 15.0 |
| Aminopropyl dimethycon | 3.0 |
| Spherical polymethyl metacrylate (average particle size 10 µm) | 2.0 |
| Trimethyl siloxycinnamate | 5.0 |
| Stearyl glycyrrhetinate | 0.1 |
| Eucalyptus oil | 3.0 |
| Perfume | q.s. |

Preparation Method

The homogeneously dissolved aqueous phase was added to the homogeneously dispersed oil phase and the mixture homogeneously dispersed by a homomixer to obtain an emulsion.

Example II-15

Cosmetic Water (with Powder)

| | % by weight |
|---|---|
| Ethanol | 30.0 |
| Isopropyl alcohol | 10.0 |
| Glycerin | 1.0 |
| Sorbitol | 1.0 |
| 3-O-ethyl ascorbic acid | 1.0 |
| POE(20)oleyl alcohol ester | 0.5 |
| Citric acid | 0.1 |
| Sodium citrate | 0.4 |
| Spherical anhydrous silicate (average particle size 1 μm) | 0.5 |
| Polyvinyl pyrrolidone | 0.01 |
| Camphor | 0.5 |
| Disodium edetate | 0.1 |
| Zinc white | 0.5 |
| Allatoin | 0.1 |
| Perfume | 0.1 |
| Purified water | Balance |

Preparation Method

The powder was homogeneously dispersed in part of the water and then added to the remainder.

Example II-16

Pack

| Formulation | % by weight |
|---|---|
| (Aqueous phase) | |
| 1,3-butylene glycol | 10.0 |
| Sorbitol | 5.0 |
| Propylene glycol | 3.0 |
| Sodium metaphosphate | 0.1 |
| Trisodium edetate | 0.1 |
| 3-O-ethyl ascorbic acid | 1.0 |
| Peony root extract | 0.1 |
| (Powder phase) | |
| Zinc oxide | 5.0 |
| Kaolin | 3.0 |
| Bentonite | 3.0 |
| Titanium oxide | 1.0 |
| (Alcohol phase) | |
| Ethanol | 5.0 |
| Caustic potash | 0.2 |
| Ethyl paraben | 0.1 |

Preparation Method

The powder phase was added to the aqueous phase and homogeneously mixed, then the alcohol phase was added and the mixture further homogeneously mixed.

Example II-17

Cream

| | % by weight |
|---|---|
| (Oil phase) | |
| Retinol | 0.2 |
| BHT | 0.1 |
| Pentaerythritol tetra-2-ethylhexanoate | 20.0 |
| Behenyl alcohol | 1.5 |
| Ethyl paraben | 0.1 |
| Butyl paraben | 0.1 |
| (Aqueous phase) | |
| Trisodium edetate | 0.1 |
| 3-O-ethyl ascorbic acid | 1.0 |
| Glycerin | 5.0 |
| POE(20)behenyl ether | 3.0 |
| Purified water | Balance |

Preparation Method

The homogeneously dissolved aqueous phase parts were added to the homogeneously dispersed oil phase parts and the mixture homogeneously dispersed by a homomixer.

Example II-18

Cream

| | % by weight |
|---|---|
| (Oil phase) | |
| Benton 38 (National Red Co.) | 2.0 |
| Diglyceryl diisostearate | 1.0 |
| Cyclomethycon | 10.0 |
| Vaseline | 5.0 |
| Squalane | 15.0 |
| Perfume | q.s. |
| Retinol | 0.1 |
| (Aqueous phase) | |
| Dipropylene glycol | 5.0 |
| Methyl paraben | 0.2 |
| Arginine | 0.1 |
| 3-O-ethyl ascorbic acid | 1.0 |
| Purified water | Balance |

Preparation Method

The homogeneously dissolved aqueous phase was added to the homogeneously mixed oil phase and the mixture homogeneously mixed by a homomixer.

Example II-19

Emulsion

| | % by weight |
|---|---|
| (Oil phase) | |
| Stearyl alcohol | 1.0 |
| Squalane | 3.0 |
| Dimethyl polysiloxane | 3.0 |

-continued

|  | % by weight |
|---|---|
| Trioctanoin | 1.0 |
| Isostearyl isostearate | 0.5 |
| Perfume | q.s. |
| (Aqueous phase) | |
| Glycerin | 5.0 |
| Dipropylene glycol | 2.0 |
| Sorbitol | 3.0 |
| 3-O-ethyl ascorbic acid | 1.0 |
| Carboxyvinyl polymer | 0.3 |
| Acrylic acid-alkyl metacrylate copolymer | 0.1 |
| Disodium edetate | 0.1 |
| Polyacrylamide | 0.5 |
| Sodium polyacrylate | 0.5 |
| Caustic potash | 0.1 |
| Citric acid | 0.1 |
| Sodium citrate | 0.2 |

Preparation Method

The homogeneously dissolved aqueous phase parts were added to the homogeneously mixed oil phase parts and the mixture homogeneously mixed by a homomixer.

As explained above, the present invention found for the first time a darkening phenomenon of skin due to UVA arising in melanin produced by colorless transparent dihydroxyindole compounds produced by melanocytes present in the basal layer of epidermis being directly struck by UVA is inhibited by 3-O-ethyl ascorbic acid, and therefore, provides an external skin treatment composition which enables the effective prevention of darkening of the skin due to UVA.

What is claimed is:

1. A method of inhibiting melanization of melanin monomers in a skin caused by irradiating the melanin monomers with ultraviolet rays having a wavelength of 320–400 nm comprising applying, to the skin, an external skin treatment composition containing a melanization inhibitor for melanin monomers.

2. A method of inhibiting melanization as claimed in claim 1, wherein said melanization inhibitor is vitamin C or its derivative.

3. A method of inhibiting polymerization of a biological dihydroxyindole compound in a skin caused by the irradiation of long wavelength ultraviolet rays having a wavelength of 320–400 nm by applying, to the skin, an external skin treatment composition comprising 3-O-ethyl ascorbic acid.

4. A method of inhibiting melanization as claimed in claim 1, wherein said derivative of vitamin C is ascorbate-2-O-α-glucoside or 3-O-ethyl ascorbic acid.

5. A method of inhibiting melanization as claimed in claim 1, wherein the vitamin C or its derivative is included in an amount of 0.001 to 50% by weight of the total weight of the external skin treatment composition.

6. A method of inhibiting polymerization the darkening of the skin as claimed in claim 3, wherein the 3-O-ethyl ascorbic acid is included in an amount of 0.001 to 50% by weight of the total weight of the external skin treatment composition.

* * * * *